United States Patent
Ochi et al.

(10) Patent No.: US 8,246,536 B2
(45) Date of Patent: Aug. 21, 2012

(54) TREATMENT TOOL INSERTION CHANNEL OF ENDOSCOPE

(75) Inventors: Kunitaka Ochi, Tokyo (JP); Yoshinori Fujii, Saitama (JP); Naoki Tanaka, Saitama (JP); Kikuo Iwasaka, Saitama (JP); Satoru Kaneda, Miyagi (JP)

(73) Assignee: Hoya Corporation, Tokyo (JP)

( * ) Notice: Subject to any disclaimer, the term of this patent is extended or adjusted under 35 U.S.C. 154(b) by 927 days.

(21) Appl. No.: 11/739,127

(22) Filed: Apr. 24, 2007

(65) Prior Publication Data

US 2007/0255105 A1 Nov. 1, 2007

(30) Foreign Application Priority Data

Apr. 26, 2006 (JP) ................................. 2006-121599
Aug. 30, 2006 (JP) ................................. 2006-233029

(51) Int. Cl.
*A61B 1/00* (2006.01)
*A61B 1/04* (2006.01)
*A61M 25/00* (2006.01)
(52) U.S. Cl. ......... 600/123; 600/139; 600/153; 604/525
(58) Field of Classification Search .................. 600/139, 600/140, 144, 146, 153; 604/523, 524, 525, 604/526, 527
See application file for complete search history.

(56) References Cited

U.S. PATENT DOCUMENTS

| | | | | |
|---|---|---|---|---|
| 4,236,509 A | * | 12/1980 | Takahashi et al. | 600/139 |
| 4,967,732 A | * | 11/1990 | Inoue | 600/139 |
| 5,378,234 A | * | 1/1995 | Hammerslag et al. | 604/95.04 |
| 5,769,830 A | * | 6/1998 | Parker | 604/528 |
| 5,873,866 A | * | 2/1999 | Kondo et al. | 604/526 |
| 5,911,715 A | * | 6/1999 | Berg et al. | 604/525 |
| 6,093,195 A | | 7/2000 | Ouchi | |
| 6,261,284 B1 | | 7/2001 | Ouchi | |
| 6,648,874 B2 | * | 11/2003 | Parisi et al. | 604/525 |
| 2001/0004676 A1 | | 6/2001 | Ouchi | |
| 2006/0178669 A1 | | 8/2006 | Sugita et al. | |

FOREIGN PATENT DOCUMENTS

| | | |
|---|---|---|
| JP | 52-17998 | 4/1977 |
| JP | 57-79501 | 5/1982 |
| JP | 62-039706 | 3/1987 |

(Continued)

OTHER PUBLICATIONS

Japan Office action, dated Jul. 27, 2011 along with an english translation thereof.

(Continued)

*Primary Examiner* — Anhtuan Nguyen
*Assistant Examiner* — Alireza Nia
(74) *Attorney, Agent, or Firm* — Greenblum & Bernstein P.L.C.

(57) ABSTRACT

A treatment tool insertion channel of an endoscope, which is arranged through an inside of an insertion part that includes a flexible tube and a bendable part, includes a flexible inner tube, a spiral groove formed around the flexible inner tube over an entire length of the bendable part and the flexible tube, at least one coil wound along a bottom of the spiral groove, and at least one type of filler with which the spiral groove is filled. The treatment tool insertion channel includes a first portion that includes a part inside the bendable part and a second portion at a proximal end side of the first portion, the first portion being configured more flexible than the second portion.

11 Claims, 11 Drawing Sheets

FOREIGN PATENT DOCUMENTS

| | | |
|---|---|---|
| JP | 2-118502 | 9/1990 |
| JP | 5-184534 | 7/1993 |
| JP | 6-041701 | 6/1994 |
| JP | 11-137509 | 5/1999 |
| JP | 11-262470 | 9/1999 |
| JP | 2000-197704 | 7/2000 |
| JP | 2002-360504 | 12/2002 |
| JP | 2007-289467 | 11/2007 |
| WO | 2005/021061 | 3/2005 |

OTHER PUBLICATIONS

Japan Office action, dated Jun. 15, 2011 along with an english translation thereof.

* cited by examiner

TREATMENT TOOL INSERTION CHANNEL OF ENDOSCOPE

BACKGROUND OF THE INVENTION

The present invention relates to a treatment tool insertion channel of an endoscope.

In general, there are provided to an insertion part of an endoscope a flexible tube and a bendable part linked with a distal end of the flexible tube so as to be bent by a remote control operation. In addition, there are arranged over the entire length of an inner space of the flexible tube and bendable part a treatment tool insertion channel configured such that a treatment tool is inserted thereinto and ejected therefrom.

Further, the treatment tool insertion channel is configured with a front portion (supple portion) thereof that includes an entire part located inside the bendable part being more flexible than a rear portion thereof such that the bendable part can smoothly be bent with a smaller curvature radius by a larger angle than the flexible tube.

In this regard, however, when the supple portion is merely formed from a supple flexible inner tube, the supple portion can easily be buckled due to an operation of bending the bendable part. Meanwhile, when the supple portion is formed with a large wall thickness, other elements such as an optical fiber bundle to be incorporated in the insertion part have to be formed with a small cross-sectional area. Thereby, basic performance of the endoscope is inevitably sacrificed.

In order to solve the aforementioned problems, conventionally, a spiral groove is provided on an outer circumferential surface of the part of the supple portion inside the bendable part such that the treatment tool insertion channel can be bent by a small force. In addition, a metal coil with spring characteristics is wound along a bottom of the spiral groove such that the treatment tool insertion channel cannot be buckled even though the bendable part is repeatedly bent (for example, see Japanese Utility Model Provisional Publication No. HEI 6-41701).

Additional, according to another conventional treatment tool insertion channel, the metal coil, which is wound along the bottom on the spiral groove formed around the part of the supple portion inside the bendable part, is extended rearward, and is wound on an outer circumferential surface of the flexible inner tube over the entire length of the supple portion that includes even a rear-side part without the spiral groove formed therearound as well as the front-side part (the part inside the bendable part) with the spiral groove formed therearound (for example, see Japanese Utility Model Provisional Publication No. SHO 62-39706).

However, according to the treatment tool insertion channel that is configured with the metal coil being wound along the bottom of the spiral groove formed on the outer circumferential surface of the front-side part of the supple portion inside the bendable part, when the flexible tube at the rear of the bendable part is bent with a small curvature radius, a rear portion of the treatment tool insertion channel without the metal coil wound therearound might be buckled.

In the meantime, when the metal coil is wound even on the outer circumferential surface of the rear-side part without the spiral groove formed therearound, the outer diameter of the entire treatment tool insertion channel is significantly enlarged. Therefore, other elements such as the optical fiber bundle to be incorporated in the insertion part have to be formed with a small cross-sectional area, and the basic performance of the endoscope is thereby sacrificed.

Further, when the supple portion is configured more flexible than the flexible portion with the spiral groove being formed only around the supple portion, mechanical characteristics are significantly different between the supple portion and the flexible portion. Therefore, there are caused problems that it is difficult to adapt both of the supple portion and the flexible portion in optimum flexibility conditions such that the treatment tool insertion channel is not easily buckled even at a border portion between the supple portion and the flexible portion.

SUMMARY OF THE INVENTION

The present invention is advantageous in that there can be provided an improved treatment tool insertion channel of an endoscope configured such that any portion thereof is hard to be buckled even trough the treatment tool insertion channel is bent, and such that the outer diameter thereof is so small over the entire length thereof that elements required for satisfying endoscope performance can be incorporated in an insertion part of the endoscope.

According to an aspect of the present invention, there is provided a treatment tool insertion channel of an endoscope, which is arranged through an inside of an insertion part of an endoscope, the insertion part including a flexible tube and a bendable part linked with a distal end of the flexible tube, the treatment tool insertion channel including a flexible inner tube, a spiral groove formed around the flexible inner tube over an entire length of the bendable part and the flexible tube, at least one coil wound along a bottom of the spiral groove around the flexible inner tube, and at least one type of filler with which the spiral groove is filled. The treatment tool insertion channel includes a first portion that includes a part inside the bendable part and a second portion at a proximal end side of the first portion, the first portion being configured more flexible than the second portion.

Optionally, the at least one coil may doubly be wound along the bottom of the spiral groove of a border portion between the first portion and the second portion.

Optionally, the at least one coil may include an all-range coil and a border coil. In this case, the all-range coil may be wound along the bottom of the spiral groove around the flexible inner tube over the entire length of the bendable part and the flexible tube, and the border coil may be wound along the bottom of the spiral groove of the border portion between the first portion and the second portion.

Alternatively or optionally, the at least one coil may include a front coil and a rear coil. In this case, the front coil may be wound along the bottom of the spiral groove of the first portion, and the rear coil may be wound along the bottom of the spiral groove of the second portion. Further, both of the front coil and the rear coil may be wound along the bottom of the spiral groove of the border portion between the first portion and the second portion.

Optionally, the at least one coil may be formed from a stainless steel wire.

Optionally, the at least one type of filler may include first filler and second filler configured harder than the first filler. In this case, the spiral groove of the first portion may be filled with the first filler, and the spiral groove of the second portion may be filled with the second filler. Further, the spiral groove of the border portion between the first portion and the second portion may be filled with the first filler and the second filler, between which a ratio is gradually changed such that a part of the border portion that is closer to the first portion is more flexible.

Yet optionally, when the first filler and the second filler are made of a same type of material, the spiral groove of the border portion may be filled with mixed filler of the first filler and the second filler, between which a mixing ratio is gradually changed such that a part of the border portion that is closer to the first portion is more flexible.

Optionally, the at least one type of filler may include at least one of silicon filler, polyurethane filler, fluorocarbon filler, and polyester filler.

Optionally, the first portion may be configured more flexible than the second portion with at least one of a depth and a pitch of the spiral groove being changed between the first portion and the second portion.

Optionally, the at least one of the depth and the pitch of the spiral groove may gradually be changed around a border portion between the first portion and the second portion.

BRIEF DESCRIPTION OF THE ACCOMPANYING DRAWINGS

FIG. 1 is a side view schematically showing an entire configuration of an endoscope in a first embodiment according to one or more aspects of the present invention.

FIG. 2 schematically shows an entire configuration of a treatment tool insertion channel of the endoscope according to one or more aspects of the present invention.

Figure 9:
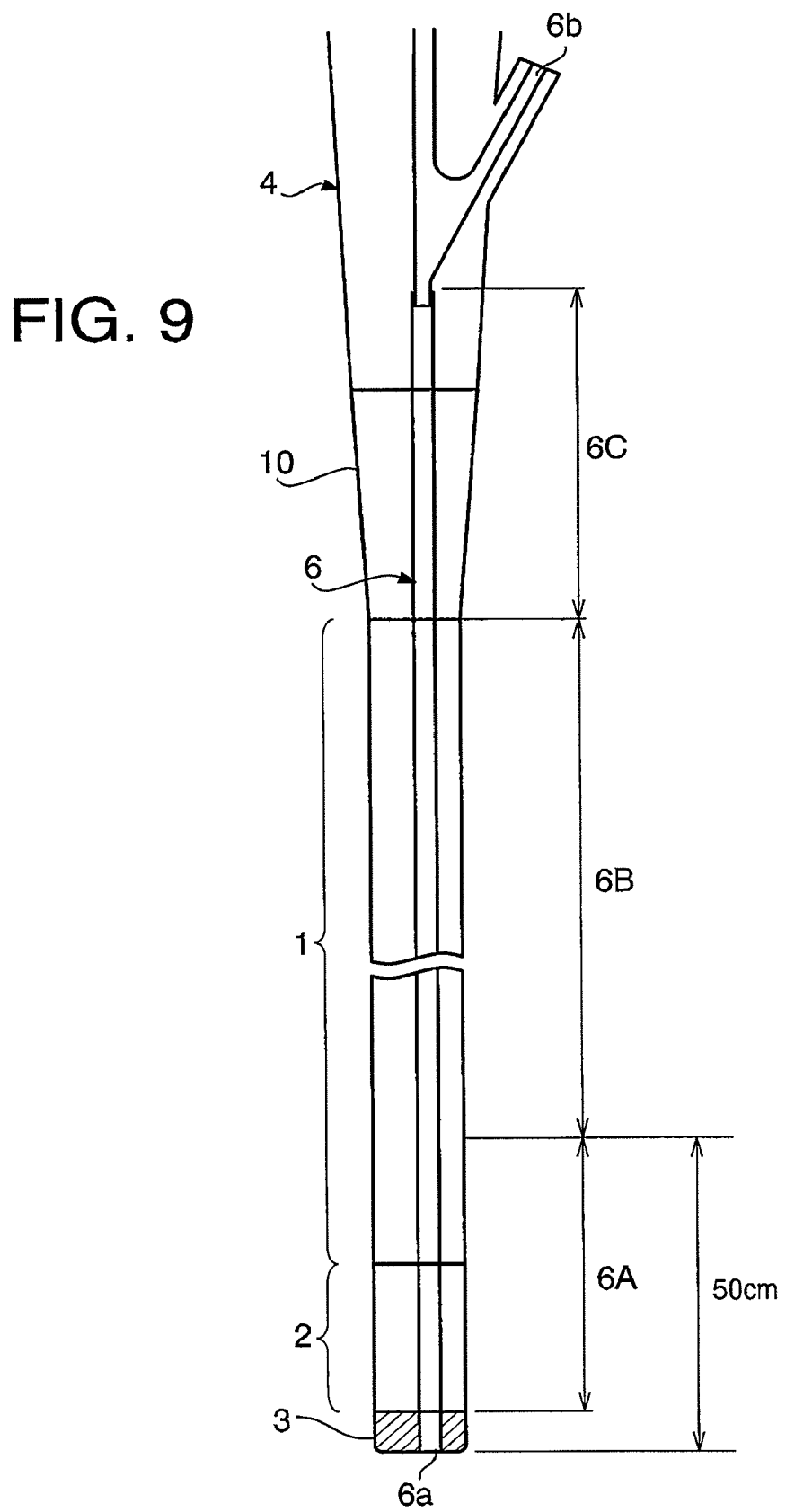

FIG. 9 schematically shows an entire configuration of a treatment tool insertion channel of an endoscope in a fifth embodiment according to one or more aspects of the present invention.

Figure 10:
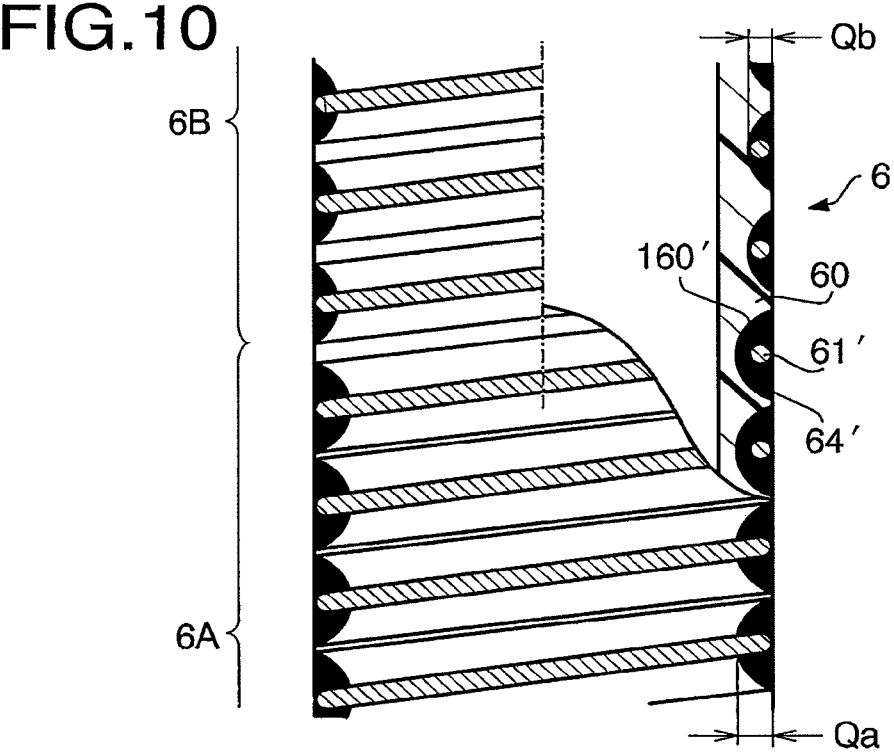

FIG. 10 is a cross-sectional partial side view of a border area between a supple portion and a flexible portion of a treatment tool insertion channel of an endoscope in the fifth embodiment according to one or more aspects of the present invention.

Figure 11:
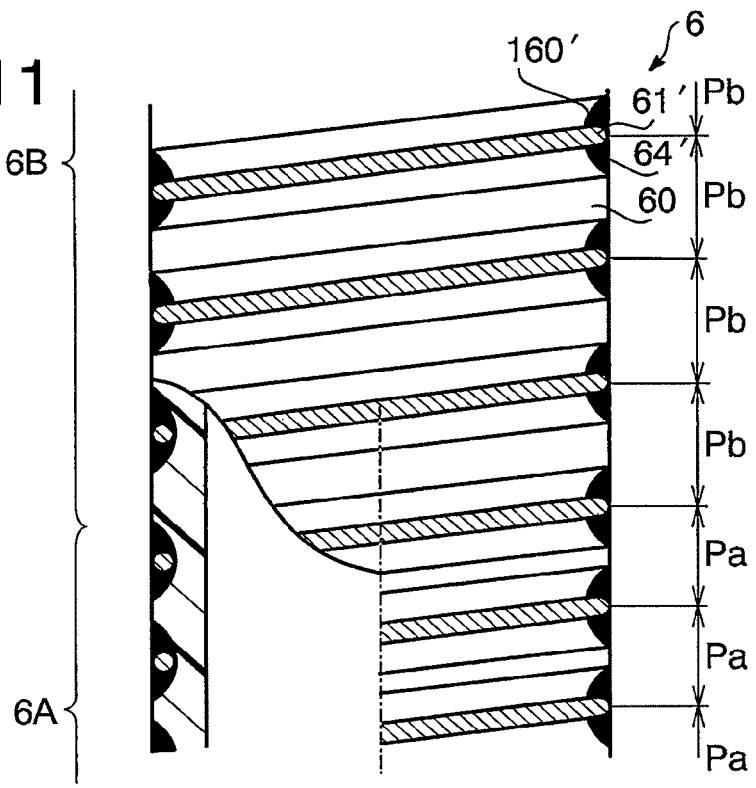

FIG. 11 is a cross-sectional partial side view of a border area between a supple portion and a flexible portion of a treatment tool insertion channel of an endoscope in a sixth embodiment according to one or more aspects of the present invention.

Figure 12:
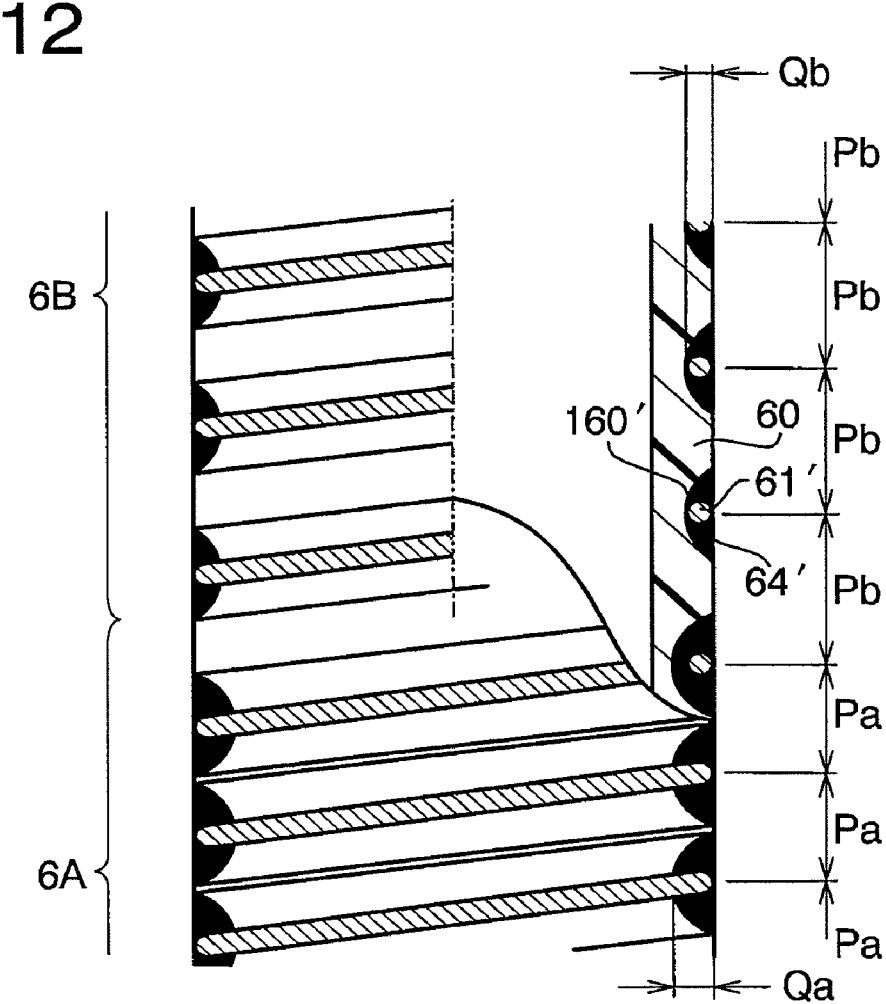

FIG. 12 is a cross-sectional partial side view of a border area between a supple portion and a flexible portion of a treatment tool insertion channel of an endoscope in a seventh embodiment according to one or more aspects of the present invention.

DETAILED DESCRIPTION OF THE EMBODIMENTS

Hereinafter, embodiments according to the present invention will be described with reference to the accompanying drawings.

Figure 1:
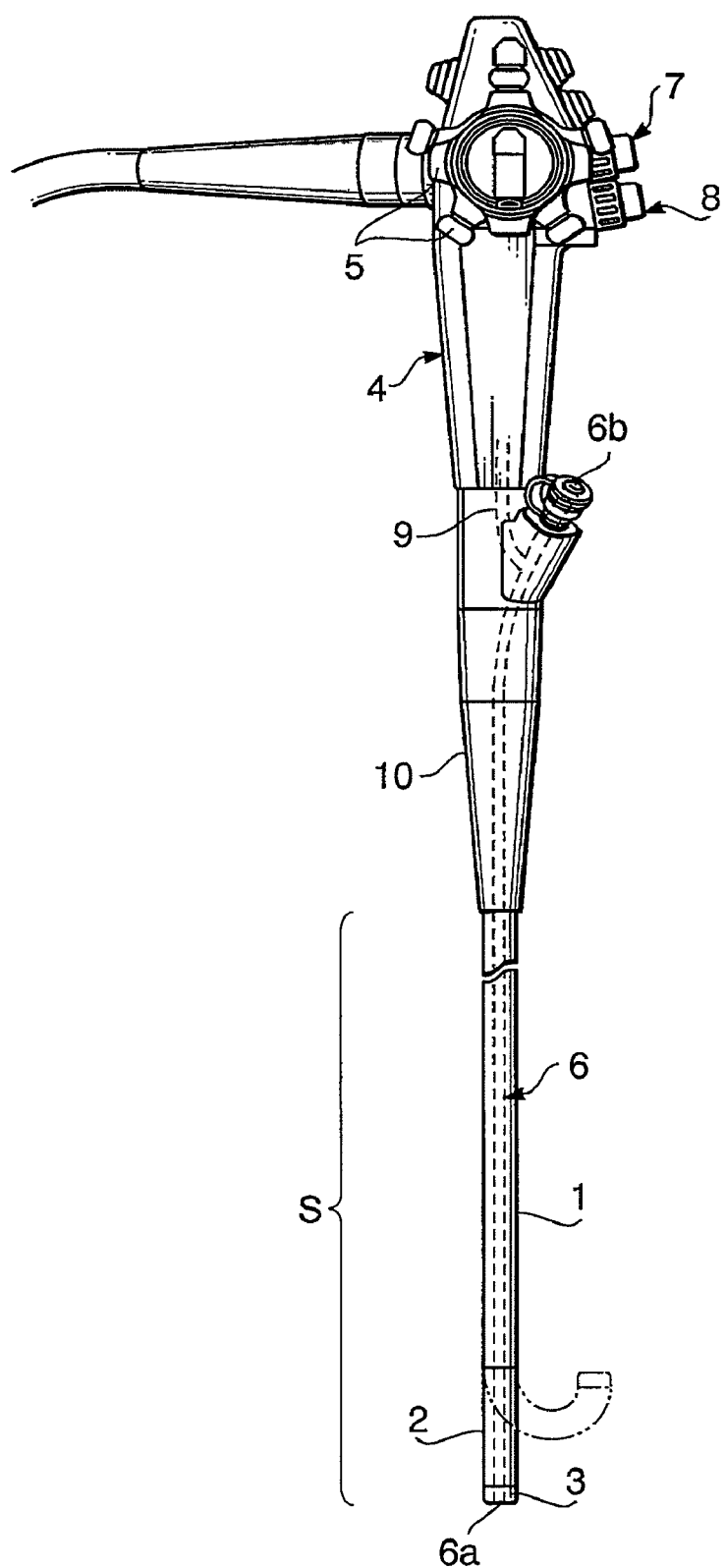

FIG. 1 is an entire configuration of an endoscope. A bendable part 2, linked with a distal end of a flexible tube 1 of an insertion part S that is freely bent by an external force, can be bent with a small curvature radius as shown by a chain double dashed line in an intended direction by an intended angle by a remote control from an operating unit 4 linked with a rear anchor of the flexible tube 1.

A distal end body 3 in which an observation port, a lighting window, and the like are arranged is linked with the distal end of the bendable part 2. The insertion part S is configured with the flexible tube 1, the bendable part 2, and the distal end body 3. A treatment tool insertion channel 6, configured such that a treatment tool is inserted thereinto and ejected therefrom, is inserted into the bendable part 2 and the flexible tube 1, and is arranged over an entire length of an inner space of them. A treatment tool inlet port 6b is arranged at a lower half portion of the operating unit 4 that is located close to a joint portion between the operating unit 4 and the flexible tube 1. A treatment tool outlet port 6a is arranged at the distal end body 3.

There are arranged at the operating unit 4 a suction operation valve 7 and an air and water supply operation valve 8 as well as a bendable part operating knob 5 for a operation of bending the bendable part 2. The suction operation valve 7 communicates with the treatment tool insertion channel 6 inside the operating unit 4 via a suction communicating tube 9.

Figure 2:
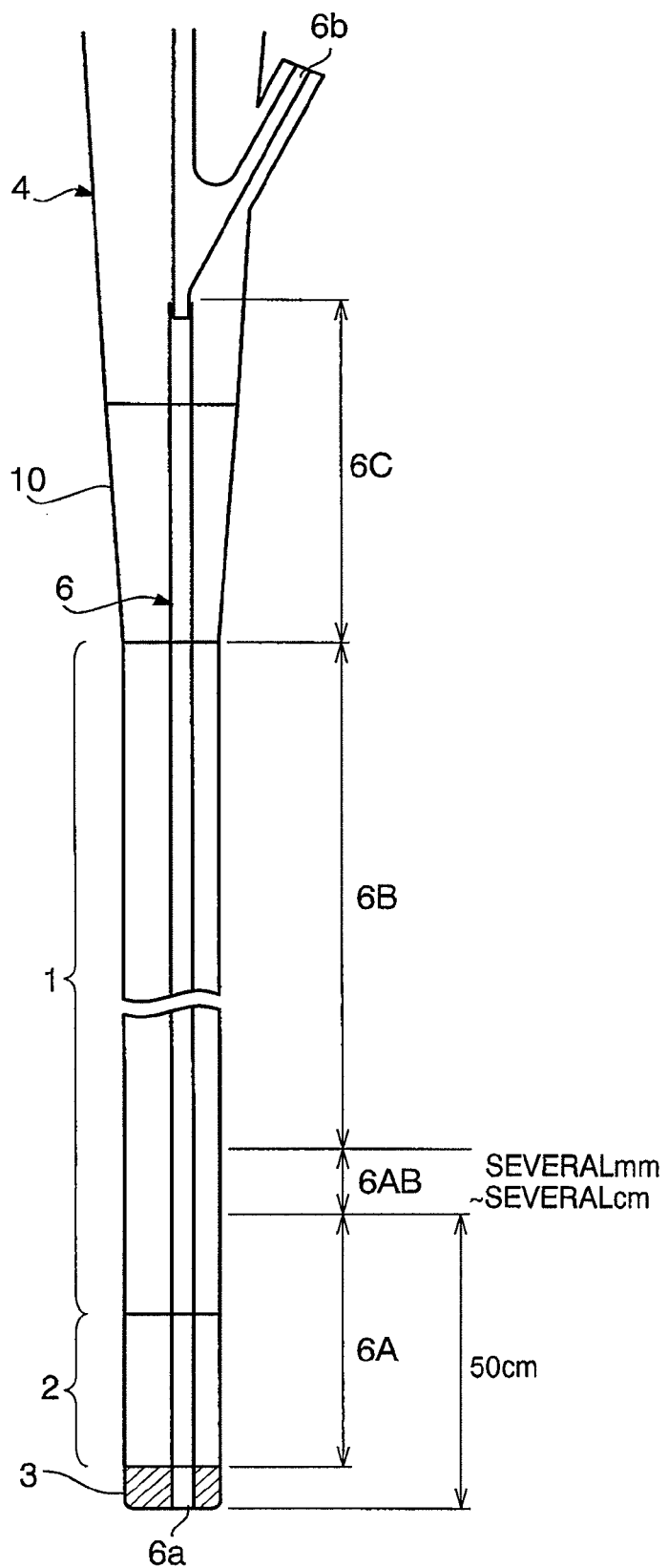

As shown in FIG. 2, the treatment tool insertion channel 6 is arranged over the entire length of the inner space of the bendable part 2 and the flexible tube 1, and a proximal end thereof runs up to an inside of the operating unit 4. In addition, the treatment tool insertion channel 6 includes a supple portion 6A, a flexible portion 6B, and a border portion 6AB. The supple portion 6A is a front-side portion located within a range of, for example, about 50 cm from a leading edge of the insertion part 1, 2, and 3 (i.e., from a leading edge of the distal end body 3), and includes an entire portion of the treatment tool insertion channel 6 that is located inside the bendable part 2. The flexible portion 6B is located at a rear side of the supple portion 6A, and is less flexible than the supple portion 6A. The border portion 6AB is located within a range of several millimeters to several centimeters between the supple portion 6A and the flexible portion 6B, and flexibility thereof gradually varies at the border portion 6AB. The treatment tool insertion channel 6 further includes a rigid portion 6C located inside the operating unit 4 and a bush 10 that is a border portion between the insertion part 1, 2, and 3 and the operating unit 4.

Figure 3:
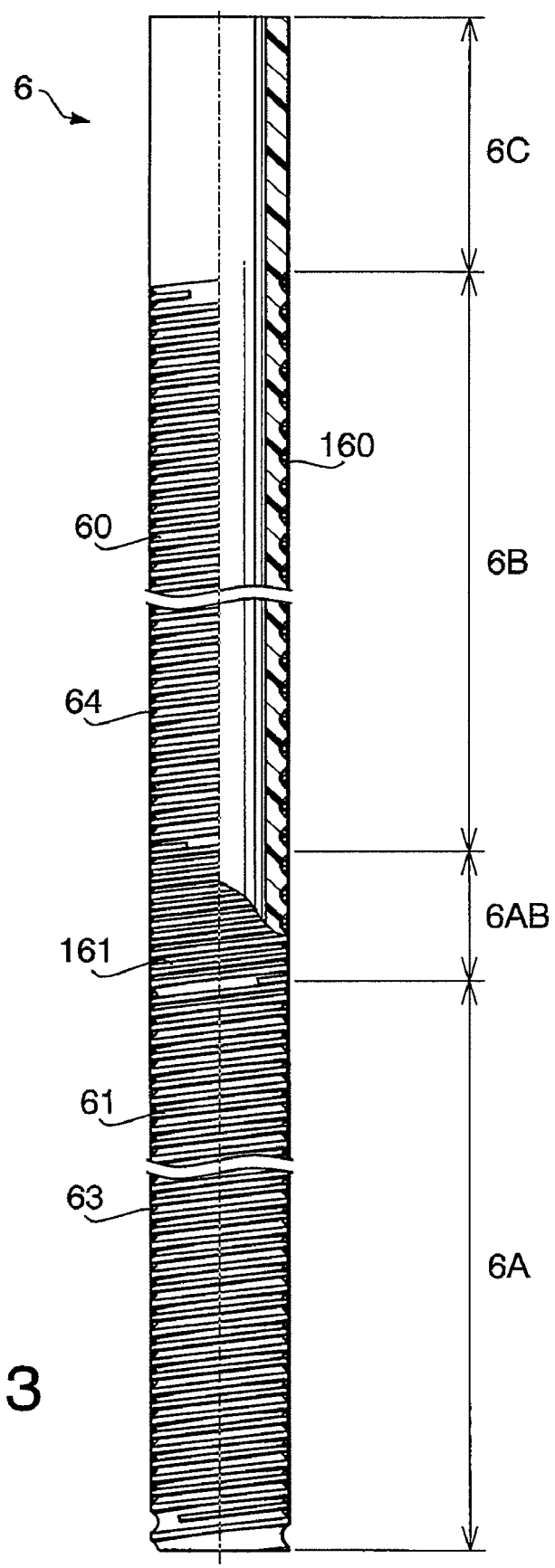
FIG. 3 is the cross-sectional partial side view of the treatment tool insertion channel of the endoscope in the first embodiment according to one or more aspects of the present invention.
Figure 4:
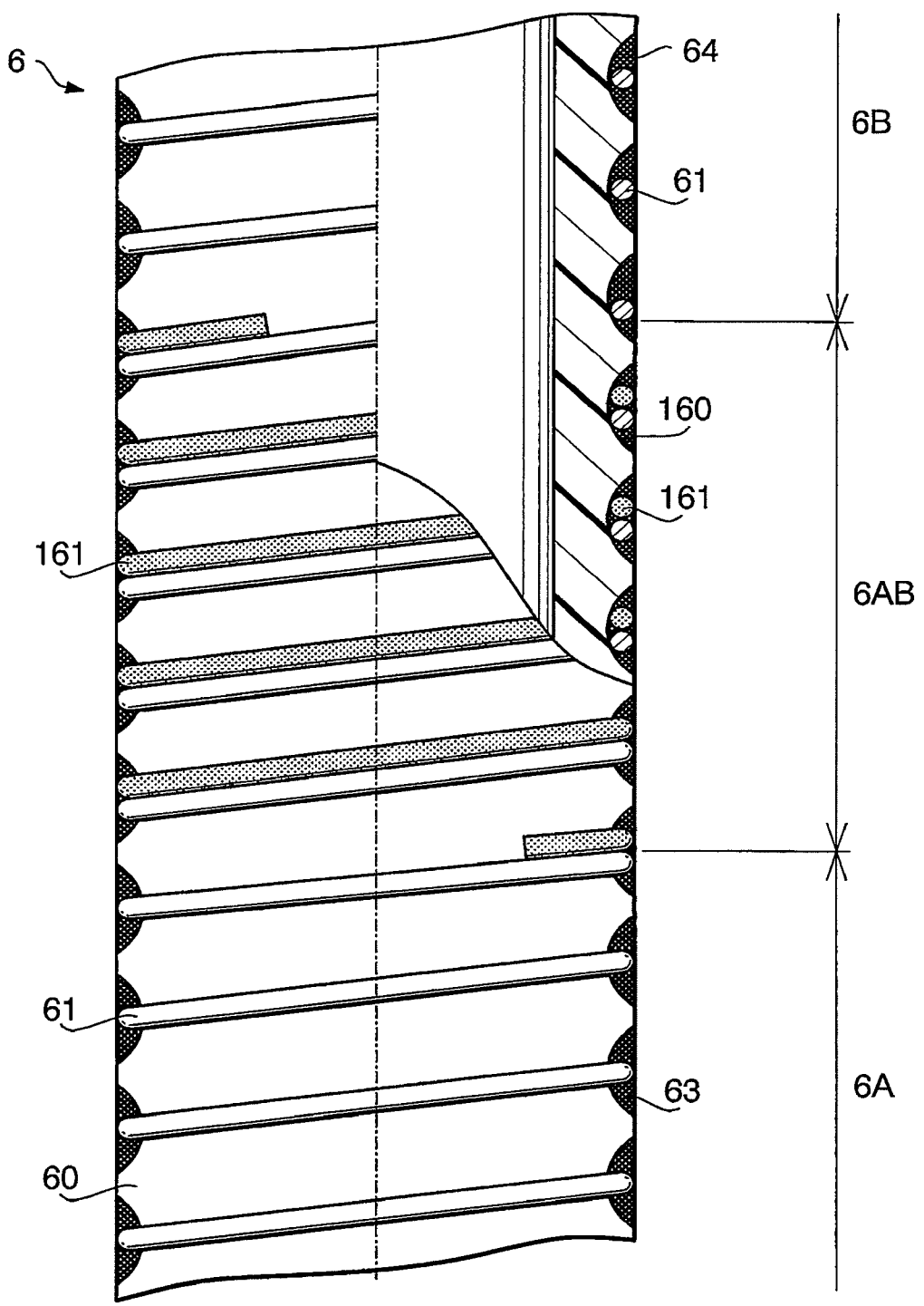
FIG. 4 is a partially enlarged illustration of a cross-sectional partial side view of the treatment tool insertion channel of the endoscope in the first embodiment according to one or more aspects of the present invention.

FIG. 3 shows a concrete configuration of the treatment tool insertion channel 6 in a first embodiment according to the present invention. FIG. 4 is an enlarged view of the border portion 6AB and an area therearound. What is represented by a reference number 60 is a flexible inner tube made from smooth material such as ethylene tetrafluoride resin. There is formed a spiral groove 160 on an outer circumferential surface of the flexible inner tube over an entire range of the supple portion 6A, border portion 6AB, and flexible portion 6B that are located inside the bendable part 2 and the flexible tube 1, so as to attain very flexible characteristics of the relevant portions 6A, 6AB, and 6B. Meanwhile, the spiral groove 160 is not formed around the rigid portion 6C, and therefore the rigid portion 6C is not so flexible.

It is noted that the spiral groove 160 may concurrently be thermoformed when the flexible tube 60 is formed by extrusion molding, or may be formed by machining an outer circumferential surface of a tube formed in a simple tube shape by the extrusion molding. In addition, a part of the entire spiral groove 160 may be formed by the extrusion molding, and the other part may be formed by the machining.

An all-range coil 61 with spring characteristics, which is made from a stainless steel wire for a spring, is serially wound along a bottom of the spiral groove 160 around the flexible inner tube 60 all over the entire range of the supple portion 6A, border portion 6AB, and flexible portion 6B. Thereby, such characteristics that the flexible tube 60 is not buckled even though the treatment tool insertion channel 6 is bent with a small curvature radius can be attained without enlarging the outer diameter of the treatment tool insertion channel 6. It is noted that the all-range coil 61 is not wound around the rigid portion 6C.

The spiral groove 160 of the supple portion 6A is filled with first filler 63 that is resilient and soft. Further, the spiral groove 160 of the flexible portion 6B is filled with second filler 64 that is harder than the first filler 63. Thereby, there is much difference in the flexibility between the supple portion 6A and the flexible portion 6B of the treatment tool insertion channel 6.

It is noted that it is possible to prevent the flexible tube 60 from being buckled and to prevent the all-range coil 61 from coming off the spiral groove 160 by filling the spiral groove 160 with the first filler 63 and the second filler 64. There can be employed as the first filler 63 and the second filler 64, for example, silicon filler, polyurethane filler, fluorocarbon filler, and polyester filler.

The spiral groove 160 of the border portion 6AB is filled with both of the first filler 63 and the second filler 64 between which a ratio is gradually changed. Thereby, the treatment tool insertion channel 6 becomes less flexible gradually from the supple portion 6A to the flexible portion 6B without a drastic change in the flexibility between the supple portion 6A and the flexible portion 6B. Hence, the flexible tube 60 is prevented from being easily broken at the border portion 6AB:

It is noted that, in the embodiment, a thickness ratio between the first filler 63 and the second filler 64 is gradually changed in the spiral groove 160 to vary the ratio between the first filler 63 and the second filler 64. However, when both of the first filler 63 and the second filler 64 are categorized as the same system filler, the spiral groove 160 of the border portion 6AB is filled with a mixed filler of the first filler 63 and the second filler 64. In this case, a mixing ratio between the first filler 63 and the second filler 64 may gradually be changed.

In addition, a border portion coil 161 with spring characteristics, which is different from the all-range coil 61 and made from a stainless steel wire for a spring, is wound along the bottom of the spiral groove 160 around the flexible inner tube 60 in parallel with the all-range coil 61 over a range of the border portion 6AB. Thereby, the flexible tube 60 can be prevented from being drastically bent and easily broken at the border portion 6AB.

According to the aforementioned configuration, the treatment tool insertion channel 6 of the present invention is hard to be buckled at any portion inside the bendable part 2 and the flexible tube 1 even though being bent. Further, since it is not required to enlarge the outer diameter of the treatment tool insertion channel 6 over the entire length thereof, there can be arranged through the inside of the bendable part 2 and the flexible tube 1 elements necessary for satisfying performance of the endoscope.

Figure 5:
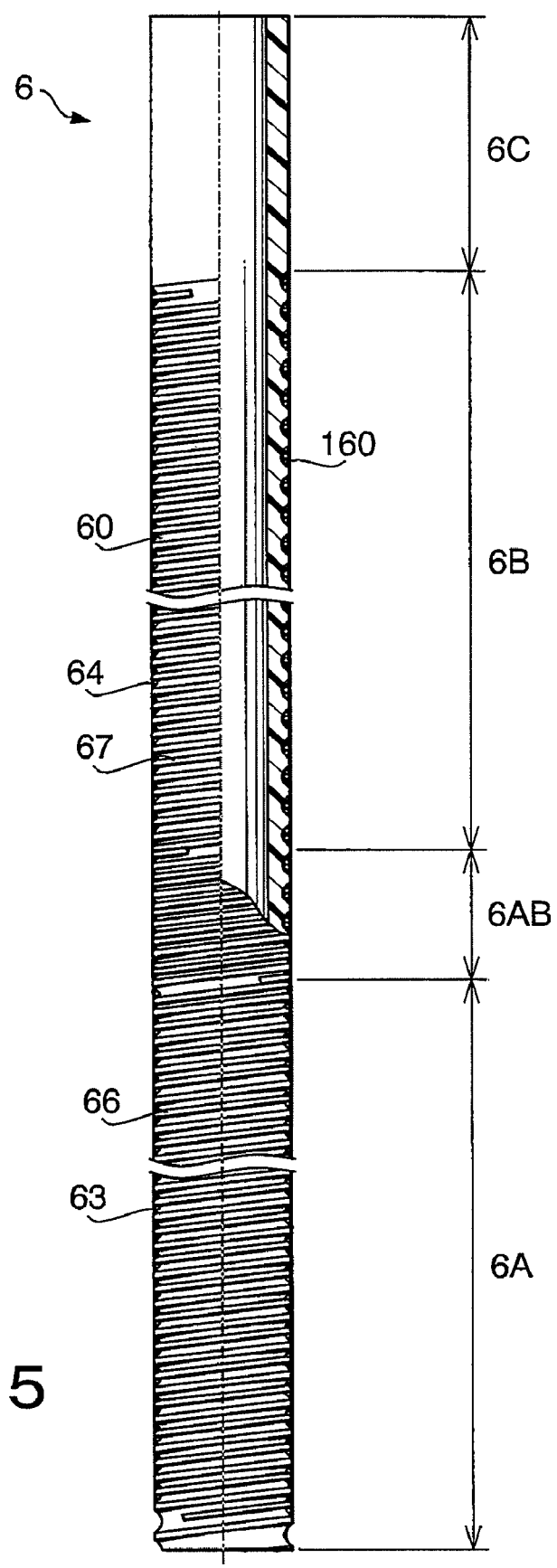
FIG. 5 is a cross-sectional partial side view of a treatment tool insertion channel of an endoscope in a second embodiment according to one or more aspects of the present invention.
Figure 6:
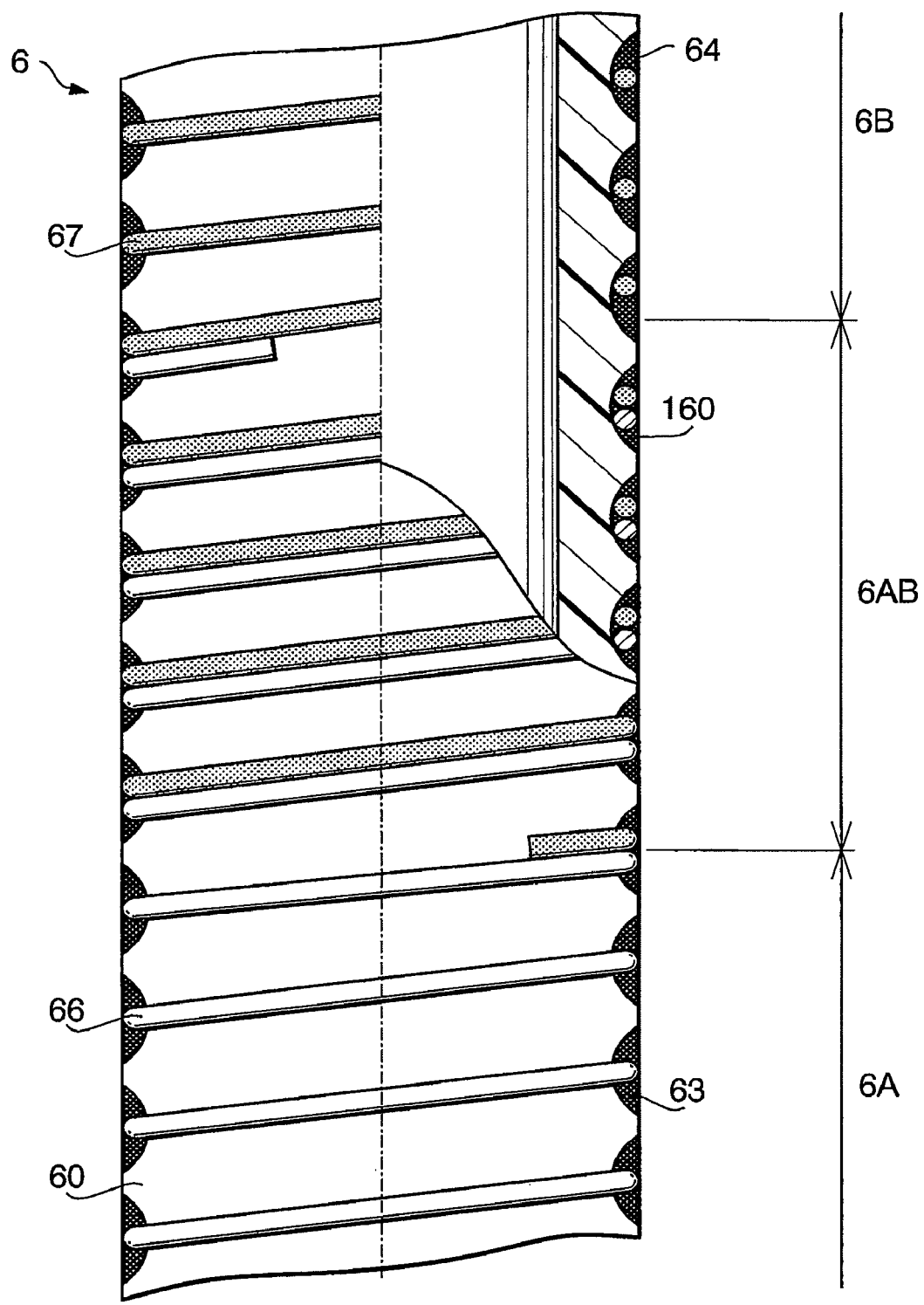
FIG. 6 is a partially enlarged illustration of the cross-sectional partial side view of the treatment tool insertion channel of the endoscope in the second embodiment according to one or more aspects of the present invention.

FIGS. 5 and 6 show a concrete configuration of the treatment tool insertion channel 6 in a second embodiment according to the present invention. In the second embodiment, a front coil 66 is serially wound along the spiral groove 160 over a range of the supple portion 6A and the border portion 6AB, and a rear coil 67 is serially wound along the spiral groove 160 over a range of the flexible portion 6B and the border portion 6AB. Consequently, at the border portion 6AB, both of the front coil 66 and the rear coil 67 are wound along the bottom of the spiral groove 160 around the flexible inner tube in parallel with each other.

The other elements of the treatment tool insertion channel 6 in the second embodiment are configured in the same manner as the aforementioned first embodiment. Therefore, the same reference numbers as the first embodiment will be assigned to the other elements in the second embodiment, and explanation regarding them will be omitted. The same effects as those brought by the first embodiment can be expected in the second embodiment. Further, a single metal coil may serially be wound along the spiral groove 160 over the entire length of the portions on which the spiral groove 160 is formed, so as to be doubly wound only at the border portion 6AB.

Figure 7:
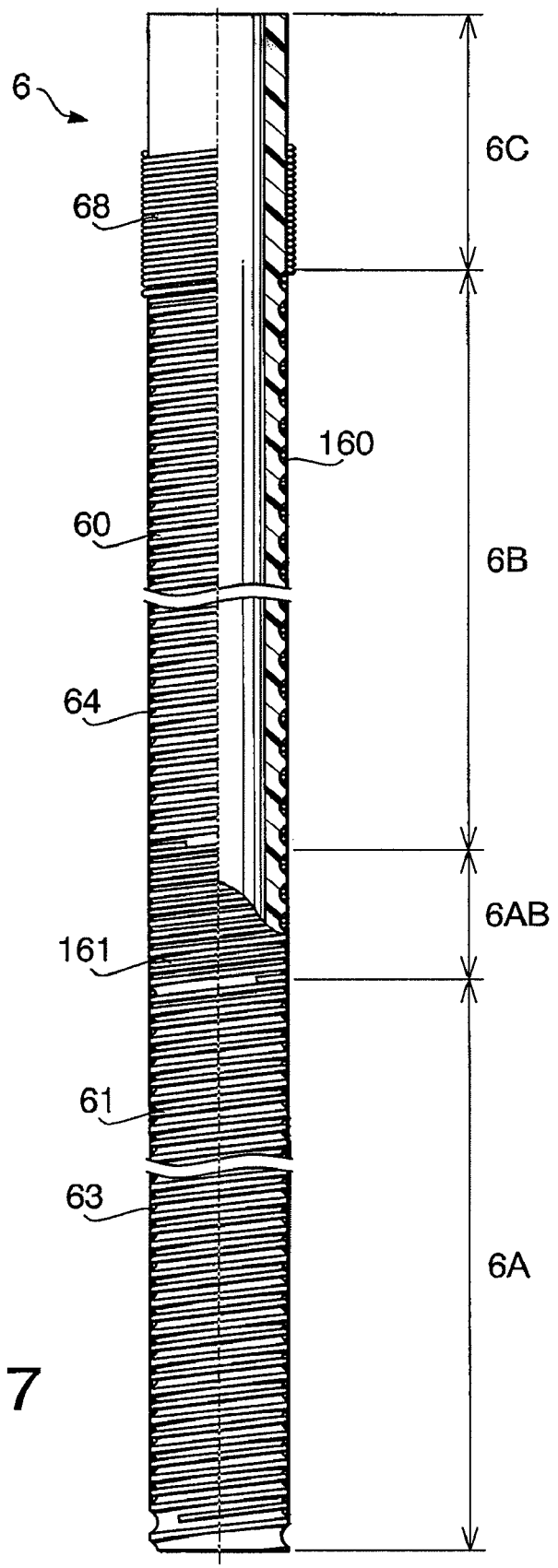
FIG. 7 is a cross-sectional partial side view of a treatment tool insertion channel of an endoscope in a third embodiment according to one or more aspects of the present invention.
Figure 8:
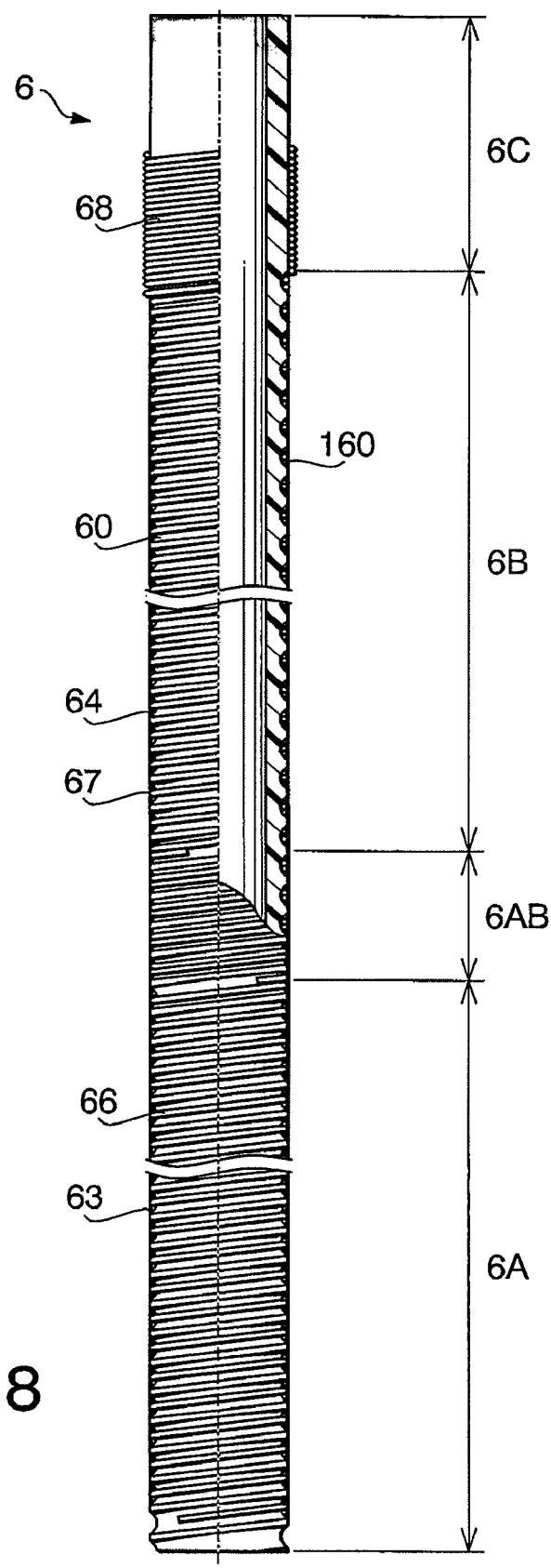
FIG. 8 is a cross-sectional partial side view of a treatment tool insertion channel of an endoscope in a fourth embodiment according to one or more aspects of the present invention.

It is noted that the rigid portion 6C of the treatment tool insertion channel 6 may be configured in any manner. For example, as shown in each of FIGS. 7 (third embodiment) and 8 (fourth embodiment), the rigid portion 6C may be configured with a metal coil 68 being wound on an outer circumferential surface of the rigid portion 6C formed in a simple tube shape in each of the aforementioned first and second embodiments. Further, although the following configuration is not shown in any drawing, the rigid portion 6C may be configured such that a metal coil is wound along the bottom of the spiral groove 160 that is formed up to the rigid portion 6C serially from the flexible portion 6B, and is partially wound even around the rigid portion 6C.

FIG. 9 schematically shows an entire configuration of a treatment tool insertion channel 6 in a fifth embodiment. As shown in FIG. 9, the treatment tool insertion channel 6, which has a configuration similar to the aforementioned embodiments, is arranged over the entire length of the inner space of the bendable part 2 and the flexible tube 1, and the proximal end thereof runs up to the inside of the operating unit 4. In addition, the treatment tool insertion channel 6 includes a supple portion 6A and a flexible portion 6B. However, the treatment tool insertion channel 6 of the fifth embodiment does not have a border portion 6AB as provided in the aforementioned embodiments. The supple portion 6A is a front-side portion located within a range of, for example, about 50 cm from the leading edge of the insertion part 1, 2, and 3 (i.e., from the leading edge of the distal end body 3), and includes the entire portion of the treatment tool insertion channel 6 that is located inside the bendable part 2. The flexible portion 6B is located at the rear side of the supple portion 6A, and is less flexible than the supple portion 6A.

The treatment tool insertion channel 6 further includes a rigid portion 6C located inside the operating unit 4 and the bush 10 that is a border portion between the insertion part 1, 2, and 3 and the operating unit 4. It is noted that the rigid portion 6C may be configured in any manner, and, for example, may be configured in the same manner as the flexible portion 6B.

FIG. 10 is an enlarged view of a border area between the supple portion 6A and the flexible portion 6B. A flexible inner tube 60 is made from smooth material such as ethylene tetrafluoride resin. There is formed a spiral groove 160' on the outer circumferential surface of the flexible inner tube over the entire range of the supple portion 6A and flexible portion 6B that are located inside the bendable part 2 and the flexible tube 1. It is noted that the spiral groove 160' may be or not be formed around the rigid portion 6C.

A stiffening coil 61' with spring characteristics, which is made from a stainless steel wire for a spring, is wound along a bottom of the spiral groove 160' around the flexible inner tube 60. The spiral groove 160' is filled with filler 64' that is made, for example, from silicon adhesive material to regulate movement of the stiffening coil 61'.

The treatment tool insertion channel 6 of the fifth embodiment is configured to have different flexibilities between the supple portion 6A and the bendable portion 6B owing to the spiral groove 160' of different depths therebetween. That is, the spiral groove 160' is configured with a depth Qa for the supple portion 6A being formed deeper than a depth Qb for the flexible portion 6B (Qa>Qb). Consequently, the supple portion 6A is more flexible than the bendable portion 6B.

Thus, since the spiral groove 160' is formed on the outer circumferential surface of the flexible inner tube 60 around both of the supple portion 6A and the flexible portion 61, mechanical characteristics are not significantly different between the supple portion 6A and the flexible portion 6B. Therefore, the treatment tool insertion channel 6 is hard to be buckled in the border area between the supple portion 6A and the flexible portion 6B. In addition, both of the supple portion 6A and the flexible portion 6B can be adapted in optimum flexibility conditions, respectively, by making the supple portion 6A and the flexible portion 6B different from each other in the depth of the spiral groove 160' thereof.

FIG. 11 is an enlarged view of a border area between a supple portion 6A and a flexible portion 6B in a sixth embodiment according to the present invention. As shown in FIG. 11, a treatment tool insertion channel 6 of the sixth embodiment is configured to have different flexibilities between the supple portion 6A and the flexible portion 6B owing to different pitches of a spiral groove 160' therebetween.

Namely, the spiral groove 160' is configured with a pitch Pa for the supple portion 6A being formed smaller than a pitch Pb for the flexible portion 6B (Pa<Pb). Consequently, the supple portion 6A is more flexible than the flexible portion 6B. Such a configuration of the sixth embodiment can bring the same effects as the fifth embodiment.

FIG. 12 is an enlarged view of a border area between a supple portion 6A and a flexible portion 6B in a seventh embodiment according to the present invention. As shown in FIG. 12, a treatment tool insertion channel 6 of the seventh embodiment is configured to have different flexibilities between the supple portion 6A and the flexible portion 6B owing to different depths and different pitches of a spiral groove 160' therebetween.

Namely, the spiral groove 160' is configured with the depth Qa for the supple portion 6A being formed deeper than the depth Qb for the flexible portion 6B (Qa>Qb) and the pitch Pa for the supple portion 6A being formed smaller than the pitch Pb for the flexible portion 6B (Pa<Pb). Consequently, the supple portion 6A is more flexible than the flexible portion 6B. Such a configuration of the seventh embodiment can bring the same effects as the fifth embodiment and the sixth embodiment.

It is noted that a treatment tool insertion channel 6 in an eighth embodiment according to the present invention may be configured as shown in FIG. 2. In the eighth embodiment, there is provided within a range of several millimeters to several centimeters between a supple portion 6A and a flexible portion 6B a border portion 6AB in which the flexibility gradually varies.

The border portion 6AB of the eighth embodiment can be formed with at least one of the depth and the pitch of the spiral groove 160' being gradually changed. Thereby, the treatment tool insertion channel 6 is hard to be buckled because of no drastic flexibility change even in the border portion 6AB between the supple portion 6A and the flexible portion 6B.

The present disclosure relates to the subject matters contained in Japanese Patent Applications No. P2006-121599 filed on Apr. 26, 2006 and No. P2006-233029 filed on Aug. 30, 2006, which are expressly incorporated herein by reference in their entireties.

What is claimed is:

1. A treatment tool insertion channel of an endoscope, which is arranged through an inside of an insertion part of an endoscope, the insertion part including a flexible tube and a bendable part linked with a distal end of the flexible tube, the treatment tool insertion channel comprising:

a flexible inner tube;

a spiral groove formed around the flexible inner tube, in an outer circumferential surface of the flexible inner tube, over an entire length of the bendable part and the flexible tube;

at least one coil wound along a bottom of the spiral groove around the flexible inner tube; and a first filler and a second filler with which the spiral groove is filled, and wherein the flexible inner tube includes a first portion that includes a part inside the bendable part and a second portion at a proximal end side of the first portion, and a border portion connecting the first portion and the second portion, the first portion being configured more flexible than the second portion, wherein the second filler is harder than the first filler, the portion of the spiral groove extending the first portion being filled with the first filler, the portion of the spiral groove extending the second portion being filled with the second filler, and the portion of the spiral groove extending the border portion being filled with mixed filler which is a mixture of the first filler and the second filler, the mixed filler being a filler in which constituents of the first filler and second filler are blended together, the first filler and the second filler being made of a same type of material, between which a blending ratio is gradually changed such that a part of the border portion that is closer to the first portion is more flexible, and wherein the at least one coil is doubly wound along a bottom of the portion of the spiral groove extending the border portion, and wherein the border portion is located within a range of several millimeters to several centimeters between the first portion and the second portion, and flexibility thereof gradually varies at the border portion.

2. The treatment tool insertion channel according to claim 1, wherein the at least one coil includes an all-range coil and a border coil, wherein the all-range coil is wound along the bottom of the spiral groove around the flexible inner tube over the entire length of the bendable part and the flexible tube, and wherein the border coil is wound along the bottom of the portion of the spiral groove extending the border portion.

3. The treatment tool insertion channel according to claim 1,
wherein the at least one coil includes a front coil and a rear coil,
wherein the front coil is wound along the bottom of the spiral groove of the first portion,
wherein the rear coil is wound along the bottom of the spiral groove of the second portion, and
wherein both of the front coil and the rear coil are wound along the bottom of the spiral groove of the border portion between the first portion and the second portion.

4. The treatment tool insertion channel according to claim 1, wherein the at least one coil is formed from a stainless steel wire.

5. The treatment tool insertion channel according to claim 1, wherein one of the first filler and the second filler includes at least one of silicon filler, polyurethane filler, fluorocarbon filler, and polyester filler.

6. The treatment tool insertion channel according to claim 1, wherein the first portion is configured more flexible than the second portion with at least one of a depth and a pitch of the spiral groove being changed between the first portion and the second portion.

7. The treatment tool insertion channel according to claim 6, wherein the at least one of the depth and the pitch of the spiral groove is gradually changed around a border portion between the first portion and the second portion.

8. The treatment tool insertion channel according to claim 6, wherein the at least one coil is formed from a stainless steel wire.

9. The treatment tool insertion channel according to claim 6, wherein the at least one type of filler includes silicon adhesive material.

10. The treatment tool insertion channel according to claim 1, wherein the border portion is defined by a plurality of adjacent spiral turns of the spiral groove, and the mixture of the first and second fillers extending the entire range of the adjacent spiral turns of the border portion.

11. The treatment tool insertion channel according to claim 10, further comprising the at least one coil including an all-range coil and a border portion coil, the border portion coil having spring characteristics which are different from the all-range coil, and the border portion coil being wound along the bottom of the spiral groove around the flexible inner tube in parallel with the all-range coil over a range of the border portion, wherein an inside diameter of the all-range coil is the same as an inside diameter of the border portion coil.

* * * * *